US011882832B2

(12) United States Patent
Brown et al.

(10) Patent No.: US 11,882,832 B2
(45) Date of Patent: *Jan. 30, 2024

(54) MULTI-TARGET ANTIMICROBIAL COMPOSITIONS COMPRISING CHITOSAN

(71) Applicant: Chinova Bioworks Inc., Fredericton (CA)

(72) Inventors: David Brown, Island View (CA); Tanzina Huq, Fredericton (CA); Natasha Dhayagude, Fredericton (CA)

(73) Assignee: CHINOVA BIOWORKS INC., Fredericton (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/940,420

(22) Filed: Sep. 8, 2022

(65) Prior Publication Data
US 2023/0142823 A1  May 11, 2023

Related U.S. Application Data

(63) Continuation of application No. 16/645,027, filed as application No. PCT/CA2018/051087 on Sep. 7, 2018, now Pat. No. 11,470,845.

(60) Provisional application No. 62/555,722, filed on Sep. 8, 2017.

(51) Int. Cl.
| | |
|---|---|
| *A01N 43/16* | (2006.01) |
| *A23L 31/00* | (2016.01) |
| *A23L 2/44* | (2006.01) |
| *A23L 3/3562* | (2006.01) |
| *A61K 8/73* | (2006.01) |
| *A61K 31/722* | (2006.01) |
| *A61Q 17/00* | (2006.01) |

(52) U.S. Cl.
CPC ............... *A01N 43/16* (2013.01); *A23L 2/44* (2013.01); *A23L 3/3562* (2013.01); *A23L 31/00* (2016.08); *A61K 8/736* (2013.01); *A61K 31/722* (2013.01); *A61Q 17/005* (2013.01); *A23V 2002/00* (2013.01)

(58) Field of Classification Search
CPC ....... A61K 31/722; A61K 8/736; A23L 31/00; A23L 33/10; A23L 33/105; A23L 2/24; A23L 3/3562; A61Q 17/005
USPC ......................................................... 514/55
See application file for complete search history.

(56) References Cited

U.S. PATENT DOCUMENTS 11,470,845 B2 * 10/2022 Brown ................. A61Q 17/005

FOREIGN PATENT DOCUMENTS

CN   106719667 A  *  5/2017  ............ A01N 43/16
WO     03077654 A1     9/2003

OTHER PUBLICATIONS

Badawy et al, Current Bioactive Compounds, 2015, 11(4), 264-273.*
International Search Report and Written Opinion of corresponding International Application No. PCT/CA2018/051087 dated Nov. 26, 2018, 5 pages.
Younes, I., et al., "Influence of acetylation degree and molecular weight of homogenous chitosans on antibacterial and antifungal activities". International Journal of Food Microbiology, Apr. 29, 2014, vol. 185, pp. 57-63.
Badaway, M.E.I., et al., "Antimicrobial activity of different molecular weight chitosans produced from shrimp shells against different plant pathogens". Current Bioactive Compounds, Sep. 29, 2015, vol. 11(4), pp. 264-273.
Zivanovic et al., "Molecular Weight of Chitosan Influences Antimicrobial Activity in Oil-in-Water Emulsions", Journal of Food Protection, vol. 67, No. 5, 2004, pp. 952-959.
Guo et al., "The influence of molecular weight of quaternized chitosan on antifungal activity", Carbohydrate Polymers 71 (2008) pp. 694-697.
Zheng et al., "Study on antimicrobial activity of chitosan with diferent molecular weights", Carbohydrate Polymers 54 (2003) pp. 527-530.
No et al., "Antibacterial activity of chitosans and chitosan oligomers with different molecular weights", International Journal of Food Microbiology 74 (2002) pp. 65-72.
Jiang et al., "Evaluation of diffusion and dilution methods to determine the antimicrobial activity of water-soluble chitosan derivatives", Journal of Applied Microbiology 114, pp. 956-963.
Kim et al., "Antimicrobial activity against foodborne pathogens of chitosan biopolymer films of different molecular weights", LWT—Food Science and Technology 44 (2011) pp. 565-569.
Shin et al., "Molecular Weight Effect on Antimicrobial Activity of Chitosan Treated Cotton Fabrics", Journal of Applied Polymer Science, vol. 80, 2495-2501 (2001).

* cited by examiner

*Primary Examiner* — Ganapathy Krishnan
(74) *Attorney, Agent, or Firm* — Bereskin & Parr LLP/S.E.N.C.R.L., s.r.l.; Patricia Folkins

(57) ABSTRACT

The present application is directed to antimicrobial compositions comprising chitosan polymers of at least two different average molecular weights (Mws), wherein the Mw of each different chitosan polymer is selected to target a different microorganism as well as method of making and using the compositions and product comprising the compositions.

12 Claims, No Drawings

MULTI-TARGET ANTIMICROBIAL COMPOSITIONS COMPRISING CHITOSAN

RELATED APPLICATIONS

The present application is a continuation of co-pending U.S. patent application Ser. No. 16/645,027 filed on Mar. 6, 2020, which is a National Stage of International Application No. PCT/CA2018/051087 filed Sep. 7, 2018, which claims the benefit of priority from U.S. Provisional Patent Application No. 62/555,722 filed on Sep. 8, 2017 the contents all of which are incorporated herein by reference.

FIELD

The present application is in the field of antimicrobial compositions, in particular natural antimicrobial compositions that target multiple microorganisms in the same product.

INTRODUCTION

The presence of microorganisms such as Gram positive and Gram negative bacteria, yeast and fungi, cause the spoilage of food, beverages, cosmetics, and personal care items, and lead to unsanitary medical devices and pharmaceuticals that poses serious risks for patients. In addition to causing health risks to the human consumer, spoilage represents wasted resources and energy, and lost revenue to producers. Preservatives reduce or eliminate microbial spoilage and are thus vital ingredients to a wide variety of products.

Natural preservative agents are growing in demand due to increased consumer awareness of the potential risks associated with artificial preservative ingredients such as benzoates and sorbates. Consumer choice increasingly deviates from products listing artificial preservatives as an ingredient. Naturally derived mushroom chitosan can inhibit a broad range of microorganisms and is well known to be a safe and natural compound. Chitosan from mushroom is especially useful for use as a preservative since it is non-animal, free of potential allergens, and can be kosher and halal.

Chitosan, a deacetylated form of the biopolymer chitin, is a widely abundant natural compound produced in the cell wall of, crustaceans, fungi, and insects. In the mushroom cell wall, chitin and chitosan provide structure to the cell by maintaining its shape and providing strength. Extraction of chitosan from mushroom biomass is relatively simple and can be considered a "green" process due to the low requirement for energy, water and other chemicals. Mushroom derived chitosan's high purity and non-animal origin present advantages for use in commercial applications such as in food and beverages, cosmetics, medical devices, and pharmaceuticals.

Mushroom chitosan is a dietary fiber that is non-toxic, highly biocompatible, and has a long history of safe use in dietary supplements, cosmetics, medical devices and pharmaceuticals.

Chitosan has been shown to be an effective antimicrobial against both Gram positive and Gram negative bacteria, yeasts and fungi. This broad range of antimicrobial effectiveness is an improvement from some other natural antimicrobials such as natamycin, which is only effective against yeast and fungi, and nisin, which is only effective against Gram positive bacteria.

The ability of chitosan to be an effective antimicrobial depends on its molecular properties including the percent degree of deacetylation (% DDA) and the molecular weight average (Mw). Generally the higher the percent degree of deacetylation the more effective the chitosan is against all types of microorganisms. More important for the effectiveness of chitosan as an antimicrobial is its Mw. Different species of microorganism are impacted differently by different types of chitosan polymer depending on the Mw of the chitosan polymer. Thus, some chitosan Mws are more effective than others at inhibiting the growth of certain types of microorganisms.

In most microbial contaminations, it is often a group of different species of microorganisms producing a deleterious effect as opposed to a single species. An ideal antimicrobial agent inhibits all of the harmful species as opposed to just a single species.

SUMMARY

The present application includes antimicrobial compositions that use naturally sourced preservatives and that are effective against multiple strains of microbial species, and that are tailorable to different microbial species combinations for different applications. The optimum Mw of chitosan polymers to be used to inhibit the growth of different types of microorganisms has been determined herein. Using this knowledge, custom antimicrobial and/or preservative compositions have been developed to target or focus on specific applications based on the abundance of each type of spoilage microorganism present or expected to be normally be present during the spoilage. Therefore compositions that contain the optimum ratio of chitosan polymer Mws for a specific product, for example, a specific food, beverage, cosmetic, personal care item, medical device, or pharmaceutical, can be prepared.

In some embodiments, the present application includes an antimicrobial composition comprising chitosan polymers of at least two different average molecular weights (Mws), wherein the Mw of each different chitosan polymer is selected to target a different microorganism.

The application further includes a method of making the compositions of the application. In some embodiments, the method comprises:
a) obtaining specific chitosan polymers having different Mws determined to be most effective at inhibiting growth of each target microorganism; and
b) combining the specific chitosan polymers having different Mws in percentage amounts based on the abundance of each type of microorganism present or expected to be present in a target product.

The present application further includes a product comprising one or more compositions of the application.

Also included in the present application is a method of inhibiting microbial growth in a product comprising incorporating an effective amount of one or more of the compositions of the application into the product as well as a method of preserving a product comprising incorporating an effective amount of one or more of the compositions of the application into the product.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DESCRIPTION OF VARIOUS EMBODIMENTS

I. Definitions

Unless otherwise indicated, the definitions and embodiments described in this and other sections are intended to be applicable to all embodiments and aspects of the present application herein described for which they are suitable as would be understood by a person skilled in the art.

The term "composition of the application" or "composition of the present application" and the like as used herein refers to a composition comprising two or more different chitosan polymers, each chitosan polymer having a different average molecular weight (Mw).

The term "average molecular weight" or "Mw" as used herein refers to the weight average molecular weight as measured in kiloDaltons (kDa) using Size Exclusion Chromatography (SEC) or Gel Permeation Chromatography (GPC).

The term "and/or" as used herein means that the listed items are present, or used, individually or in combination. In effect, this term means that "at least one of" or "one or more" of the listed items is used or present.

As used in the present application, the singular forms "a", "an" and "the" include plural references unless the content clearly dictates otherwise. For example, an embodiment including "a microorganism" should be understood to present certain aspects with one microorganism or two or more additional microorganisms.

In embodiments comprising an "additional" or "second" component, such as an additional or second microorganism, the second component as used herein is different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

As used herein, the term "effective amount" means an amount of one or more compositions of the application that is effective to achieve the desired result. For example in the context of inhibiting microbial growth, an effective amount is an amount that, for example, increases said inhibition compared to the inhibition without administration of the one or more compositions.

II. Compositions of the Application

The present application includes an antimicrobial composition comprising chitosan polymers of at least two different average molecular weights (Mws), wherein the Mw of each different chitosan polymer is selected to target a different microorganism.

In some embodiments, the Mw of each different chitosan polymer is selected to focus on or target a different microorganism known to infect a specific product. In some embodiments, the specific product is a product that is susceptible to microbial growth. In some embodiments, the product is a food product, a beverage product, a cosmetic product, a personal care item, a medical device or a pharmaceutical product. Pharmaceutical products include both prescription and over-the-counter pharmaceutical products. The product may be in any form, including liquid and solid and combinations thereof.

In some embodiments, the microorganism target for the antimicrobial compositions of the application determines how to select the amount and size of each chitosan polymer to be included. Therefore if the target microorganism is bacteria, the composition comprises substantially greater amounts in percent by weight of chitosan polymers having a Mw of about 30 kDa, about 40 kDa, about 150 kDa and/or about 170 kDa. If the bacteria are Gram positive, the composition comprises substantially greater amounts in percent by weight of chitosan polymers having a Mw of about 150 kDa and/or about 170 kDa. If the bacteria are Gram negative, the composition comprises substantially greater amounts in percent by weight of chitosan polymers having a Mw of about 30 kDa and/or about 40 kDa. If the target microorganism is yeast, the composition comprises substantially greater amounts in percent by weight of chitosan polymers having a Mw of about 20 kDa and/or about 60 kDa. If the target microorganism is mold, the composition comprises substantially greater amounts in percent by weight of chitosan polymers having a Mw of about 200 kDa.

If the target microorganisms include two of bacteria, mold and yeasts, then the antimicrobial composition comprises substantially greater amounts of chitosan polymers that target those organisms. Accordingly a composition targeting bacteria and mold will comprise substantially greater amounts in percent by weight of chitosan polymers having a Mw of about 30 kDa, about 40 kDa, about 150 kDa and/or about 170 kDa and chitosan polymers having a Mw of about 200 kDa. A composition targeting bacteria and yeast will comprise substantially greater amounts in percent by weight of chitosan polymers having a Mw of about 30 kDa, about 40 kDa, about 150 kDa and/or about 170 kDa and chitosan polymers having a Mw of about 20 kDa and/or about 60 kDa. A composition targeting yeast and mold will comprise substantially greater amounts in percent by weight of chitosan polymers having a Mw of about 20 kDa and/or about 60 kDa, and chitosan polymers having a Mw of about 200 kDa.

If the target microorganisms include all three of bacteria, mold and yeasts, then the antimicrobial composition may be a broad spectrum antimicrobial composition described in greater detail below. The percentages of each chitosan polymer will depend on which type of microorganism one wishes to target more, which may depend on, for example, a product's susceptibility to each microorganism. None-theless a person skilled in the art can determine the amounts and Mw of each chitosan polymer based on the activity data disclosed herein and knowledge of the microorganisms to target.

In some embodiments, the term "substantially greater amounts in percent by weight" means that the referenced chitosan polymer is present in the composition in amounts that are about 5 percentage points (w/w) to about 100 percentage points (w/w), or about 7 percentage points (w/w) to about 50 percentage points (w/w), or about 10 percentage points (w/w) to about 30 percentage points (w/w) greater than other chitosan polymers in the composition. For example, if the composition comprises 4 different chitosan polymers, each having a different Mw, and one chitosan polymer was present in about 20 percentage points greater than the other three, then the composition would comprise about 40% by weight of the polymer present in greater amounts and about 20% of each the remaining three polymers.

In some embodiments, the antimicrobial composition is a broad spectrum composition and comprises at least 4 different chitosan polymers each having a different Mw and each present in substantially equal percentages by weight, wherein the 4 different chitosan polymers have a Mw of:
(1) about 20 kDa or about 60 kDa;
(2) about 30 kDa or about 40 kDa;
(3) about 150 kDa or about 170 kDa; and
(4) about 200 kDa.

In some embodiments, the broad spectrum antimicrobial composition comprises substantially equal percentages by weight of chitosan polymers having a Mw of about 20 kDa, about 60 kDa, about 30, about 40 kDa, about 150 kDa, about 170 kDa, and about 200 kDa.

In some embodiments, the broad spectrum antimicrobial composition targets yeasts and comprises substantially equal percentages by weight of chitosan polymers having a Mw of:
(1) about 30 kDa or about 40 kDa;
(2) about 150 kDa or about 170 kDa; and
(3) about 200 kDa; and
(4) a substantially greater percentage by weight of a chitosan polymer having a Mw of about 20 kDa or about 60 kDa.

In some embodiments, the broad spectrum antimicrobial composition that targets yeasts comprises substantially equal percentages by weight of chitosan polymers having a Mw of about 30, about 40 kDa, about 150 kDa, about 170 kDa, and about 200 kDa, and a substantially greater percentage by weight of a chitosan polymer having a Mw of about 20 kDa and a chitosan polymer having a Mw of about 60 kDa.

In some embodiments, the broad spectrum antimicrobial composition targets mold and comprises substantially equal percentages by weight of chitosan polymers having a Mw of:
(1) about 20 kDa or about 60 kDa
(2) about 30 kDa or about 40 kDa; and
(3) about 150 kDa or about 170 kDa; and
(4) a substantially greater percentage by weight of a chitosan polymer having a Mw of about 200 kDa.

In some embodiments, the broad spectrum antimicrobial composition that targets mold comprises substantially equal percentages by weight of chitosan polymers having a Mw of about 20 kDa, about 60 kDa, about 30, about 40 kDa, about 150 kDa, and about 170 kDa, and a substantially greater percentage by weight of a chitosan polymer having a Mw of about 200 kDa.

In some embodiments, the broad spectrum antimicrobial composition targets bacteria and comprises substantially equal percentages by weight of chitosan polymers having a Mw of:
(1) about 20 kDa or about 60 kDa; and
(2) about 200 kDa; and
(3) a substantially greater percentage by weight of a chitosan polymer having a Mw of about 30 kDa or about 40 kDa; and
(4) a substantially greater percentage by weight of a chitosan polymer having a Mw of about 150 kDa or about 170 kDa In some embodiments, the broad spectrum antimicrobial composition that targets bacteria comprises substantially equal percentages by weight of chitosan polymers having a Mw of about 20, about 60 kDa and about 200 kDa; and a substantially greater percentage by weight of a chitosan polymer having a Mw of about 30 kDa and about 40 kDa, and a chitosan polymer having a Mw of about 150 kDa and about 170 kDa.

In some embodiments, the broad spectrum antimicrobial composition targets Gram positive bacteria and comprises substantially equal percentages by weight of chitosan polymers having a Mw of:
(1) about 20 kDa or about 60 kDa;
(2) about 30 kDa or about 40 kDa; and
(3) about 200 kDa; and
(4) a substantially greater percentage by weight of a chitosan polymer having a Mw of about 150 kDa or about 170 kDa In some embodiments, the broad spectrum antimicrobial composition that targets Gram positive bacteria comprises substantially equal percentages by weight of chitosan polymers having a Mw of about 20, about 60 kDa, about 30 kDa, about 40 kDa, and about 200 kDa; and a substantially greater percentage by weight of a chitosan polymer having a Mw of about 150 kDa and about 170 kDa.

In some embodiments, the broad spectrum antimicrobial composition targets gram negative bacteria and comprises substantially equal percentages by weight of chitosan polymers having a Mw of:
(1) about 20 kDa or about 60 kDa;
(2) about 150 kDa or about 170 kDa; and
(3) about 200 kDa; and
(4) a substantially greater percentage by weight of a chitosan polymer having a Mw of about 30 kDa or about 40 kDa In some embodiments, the broad spectrum antimicrobial composition that targets Gram negative bacteria comprises substantially equal percentages by weight of chitosan polymers having a Mw of about 20, about 60 kDa, about 150 kDa, about 170 kDa, and about 200 kDa; and a substantially greater percentage by weight of a chitosan polymer having a Mw of about 30 kDa and about 40 kDa.

In some embodiments, the compositions comprise two or more chitosan polymers that target two or more different types of Gram positive bacteria. For example, the antimicrobial composition comprises equal percentages by weight of chitosan polymers having a Mw of about 150 kDa and about 170 kDa to target *Lactobacillus* and *Listeria*, respectively. If the two target organisms are present in the product in unequal amounts then the amount of each chitosan polymer is adjusted accordingly.

In some embodiments, the compositions comprise two or more chitosan polymers that target two or more different types of Gram negative bacteria. For example, the antimicrobial composition comprises equal percentages by weight of chitosan polymers having a Mw of about 30 kDa and about 40 kDa to target *E. coli* and *Acetobacer*, respectively. If the two target organisms are present in the product in unequal amounts then the amount of each chitosan polymer is adjusted accordingly.

In some embodiments, the compositions comprise two or more chitosan polymers that target two or more different types of yeast. For example, the antimicrobial composition comprises equal percentages by weight of chitosan polymers having a Mw of about 20 kDa and about 60 kDa to target *Pichia* and *Saccharomyces*, respectively. If the two target organisms are present in the product in unequal amounts then the amount of each chitosan polymer is adjusted accordingly.

In some embodiments, the term "substantially equal percentages by weight" means that the referenced chitosan polymers are present in the composition in amounts that are the same within about +/−5% (wt/wt), about +/−4% (wt/wt), about +/−3% (wt/wt), about +/−2% (wt/wt) or about +/−1% (wt/wt).

In some embodiments, different Mw fractions of chitosan are isolated using chromatography, and/or by chemically, physically, or enzymatically altering the molecular weight of a chitosan polymer isolated from natural sources to obtain the desired Mw fraction.

In some embodiments, the chitosan polymer is from a fungus, crustacean or an insect. In some embodiments, the chitosan polymer is from a fungus. In some embodiments, the chitosan polymer is from a mushroom.

In some embodiments, the compositions of the application are in the form of a powder. In some embodiments, the compositions of the application are in the form of a liquid solution or suspension. In some embodiments, the solvent for the solution or suspension is water. In some embodiments, the whole composition is dissolved into a solution.

In some embodiments, the compositions of the application include further ingredients such as other preservative ingredients, other antioxidant ingredients, colors, dyes, fillers and other excipients known in the art. In some embodiments, the compositions are formulated for inclusion in a specific product and ingredients are added to facilitate this inclusion as would be known to a person skilled in the art.

III. Methods of Making Composition of the Application

The application further includes a method of making the compositions of the application. In some embodiments, the method comprises
a) obtaining specific chitosan polymers having different Mws determined to be most effective at inhibiting growth of each target microorganism; and
b) combining the specific chitosan polymers having different Mws in percentage amounts based on the abundance of each type of microorganism present or expected to be present in a target product.

In some embodiments, the chitosan polymers having different Mws are obtained by dissolving chitosan from a natural source in weak acidic solution, for example a solution of an organic acid such as acetic acid or lactic acid, and exposed for certain periods of time to a chemical which will depolymerize the chitosan. In some embodiments, alkali bases such as NaOH or KOH are used to chemically depolymerize the chitosan since the reaction occurs at a pace that allows the reaction to be stopped once the desired molecular weight has been achieved. Using an alkali base also has another benefit of deacetylating the chitosan simultaneously while depolymerization occurs. In some embodiments, strong acids such as hydrochloric acid, or highly oxidizing chemicals like hydrogen peroxide, are used to depolymerize chitosan quickly. In some embodiments, the chitosan is depolymerized using enzymes. These methods are used to isolate molecular weight fractions either the same size or smaller than the largest molecular weight present in the natural chitosan. For example, if the original natural chitosan is 200 kDa the isolated fractions are equal to or smaller than 200 kDa.

In some embodiments the chitosan polymers having different Mws are obtained by dissolving chitosan from a natural source in weak acidic solution, for example a solution of an organic acid such as acetic acid or lactic acid. In some embodiments the chitosan is dissolved in the acidic solution in amounts to allow the solution to be fluid enough to be pumped into a chromatography column. The different Mw fractions of chitosan are then isolated from the column. In some embodiments, the different Mw fractions of chitosan are isolated using other physical methods. In some embodiments, the isolated fractions of different Mws are precipitated by adjusting the pH of a solution of each fraction to >7 using a base, such as sodium or potassium hydroxide (NaOH or KOH). In some embodiments, the precipitated chitosan is collected by filtration or centrifugation and dried into a powder.

In some embodiments, the PDI of the chitosan Mw fractions is about 2 to about 3.

In some embodiments, molecular weights are analyzed by HPLC with size exclusion chromatography or gel permeation chromatography.

In some embodiments, the different Mw polymers of chitosan are combined as powders. In some embodiments, the different Mw polymers of chitosan are combined as solutions or are combined in a solution or suspension.

Obtaining chitosan polymer fractions having a desired Mw has certain challenges. Variables such as reaction time, temperature and agitation speed, and starting Mw have to be taken into consideration as each will affect the size and PDI of the resulting product. Further, there can be continued depolymerization during precipitation and collection steps which must be taken into consideration. The present Applicant has perfected this method to isolate chitosan fractions having specific desired Mw's and PDIs. To the best of the Applicant's knowledge no such methods existed previously therefore identification of the antimicrobial activity for such a wide variety of chitosan Mws has not been possible until now.

IV. Methods of Using and Product Containing Compositions of the Application

In some embodiments, the compositions of the application are used as antimicrobial agents or preservatives in products in need of such agents. In some embodiments, these products include, but are not limited to food, beverages, cosmetics, personal care items, medical devices and pharmaceuticals. As noted above, pharmaceuticals include prescription and over-the-counter pharmaceuticals. The product may be in any form, including liquid, semi-solid and solid and combinations thereof.

Accordingly, the present application further includes a product comprising one or more compositions of the application. In some embodiments, the product is a food, beverage, cosmetic, personal care item, medical device or pharmaceutical.

In some embodiments, the compositions of the application are incorporated as an ingredient or a component during the preparation of the product.

In some embodiments, the application includes a method of inhibiting microbial growth in a product comprising incorporating an effective amount of one or more of the compositions of the application into the product.

In some embodiments, the application includes a method of preserving a product comprising incorporating an effective amount of one or more of the compositions of the application into the product.

In some embodiments, the application includes a use of one or more of the compositions of the application to inhibit microbial growth in a product or to preserve a product.

In some embodiments, the effective amount of the composition of the application will depend on the identity of the product. For example, if the product is a food or beverage product an effective amount may be an amount of the composition to deliver or incorporate about 10 ppm to about 500 ppm, about 20 ppm to about 400 ppm, about 30 ppm to about 300 ppm, about 40 ppm to about 250 ppm, or about 50 ppm to about 200 ppm of the chitosan polymers of at least two different average molecular weights (Mws) to the product. In a further example, if the product is a cosmetic or personal care product an effective amount may be an amount of the composition to deliver or incorporate about 50 ppm to about 1000 ppm, about 100 ppm to about 900 ppm, about 200 ppm to about 700 ppm, about 300 ppm to about 600 ppm, or about 400 ppm to about 500 ppm of the chitosan polymers of at least two different average molecular weights (Mws) to the product.

V. Examples

Example 1: Preparation of Chitosan Polymers Having Different Mws

The chitosan molecular weight fractions were separated by chemical depolymerization using a sodium hydroxide solution. 10 g of chitosan was dissolved in 250 mL of 1% (v/v) glacial acetic acid solution at 35° C. for 5 hours. 10 mL of 0.3M sodium hydroxide was added into the chitosan solution and the solution heated to 60° C. while being stirred with a magnetic stir bar. The starting Mw was measured using GPC according to the method outlined below and depending on the starting Mw measurement the chitosan was exposed for varying amounts of time to achieve the desired Mw. Once the sufficient period of time has elapsed the reaction was stopped by adding sodium hydroxide to raise the pH above 7 in order to precipitate the chitosan and the precipitate was collected using centrifugation, rinsed with water, and dried using lyophilization. This process was repeated until each desired Mw was obtained. A general trend for the rate of the reaction was that there was a rapid period of depolymerization where the Mw decreased from approximately 200 kDa to approximately 100 kDa in 1 hour, and then a slow period where the molecular weight decreased from approximately 100 kDa to 10 kDa in over 12 hours. In this example 21 different molecular weights were produced; 3, 10, 20, 30, 40, 50, 60, 70, 80, 90, 100, 110, 120, 130, 140, 150, 160, 170, 180, 190 and 200 kDa.

The chitosan Mw fractions were analyzed by HPLC with size exclusion chromatography or gel permeation chromatography, and incorporating an oven that has four detectors: refractive index (RI), ultra-violet (UV), right angle and low angle light scattering (RALS/LALS), and four-capillary differential viscometer (VIS). Chitosan samples were dissolved in the mobile phase of 0.1M acetic acid/0.3M $NaNO_3$ for 4-6 hours on a rocker at room temperature. A concentration of chitosan at ~5-10 mg/mL was used for the samples. Columns can be used in a series and with a large range of separation efficiency. The isolated chitosan Mw's used for antimicrobial testing had a PDI between 2 and 3.

Example 4: Broad Spectrum of Antimicrobial Screening of Chitosan Fractions Having Different Mws The microorganisms *Listeria innocua* (Seeliger ATCC 33090), *Escherichia coli* (Migula ATCC 11229), *Saccharomyces cerevisiae*, *Acetobacter aceti* (Pasteur ATCC 15973), *Lactobacillus casei* (Orla-Jensen ATCC 393), *Pichia anomala* (Hansen), and *Rhizopus oryzae* were used for this experiment. The microorganisms were kept frozen at −4° C. in BHI, Luria broth and PDB containing glycerol (10% v/v). Before use, the stock cultures were resuscitated through 2 consecutive 24 h growth in Brain Heart Infusion (BHI) or Luria-Bertaini (LB) or Potato Dextrose Broth (PDB) at 37° C. to obtain the working cultures containing approximately $10^9$ CFU/mL.

The antimicrobial activity of different molecular weights of chitosan or formulations thereof were tested in vitro according to an agar diffusion assay against *Listeria innocua, Escherichia coli, Saccharomyces cerevisiae, Acetobacter aceti, Lactobacillus casei, Pichia anomala*, and *Rhizopus oryzae*. Test mediums containing BHI/LB/PDB and agar were prepared, autoclaved and allowed to cool at 50° C. in a water bath. Test mediums BHI, LB and PDB were prepared into solution prior to being autoclaved. The microorganisms were grown in BHI, LB, PDB and placed in an incubator at 37 (for bacteria) or 30° C. (for yeast and fungi) for 24 or 48 hr to get the final microbial concentration $10^9$ CFU/mL. The medium was inoculated with 1.0% (v/v) BHI or LB or PDB containing the microbial cultures ($10^9$ CFU/mL) to obtain a final microbial population of approximately $10^6$ CFU/mL. Then 1 mL of the inoculated medium was spread to each Petri dish (95 mm×15 mm). Thereafter, holes measuring 7.0 mm in diameter were dug and 80-100 μL of the antimicrobial formulations at concentration range of 10-500 ppm was added to each hole. The plates were incubated for 24 or 48 h at 37 or 30° C. for bacteria and yeast/fungi respectively. The diameter (mm) of the inhibition zones (IZ) was measured to determine the antimicrobial activity of the formulations.

The effect of fungal chitosan samples having different Mws on the growth of a variety of microorganisms was assessed. In particular, the growth of various representative microbial organisms was observed in the presence of fungal chitosan samples having molecular weights of 3, 10, 20, 30, 40, 50, 60, 70, 80, 90, 100, 110, 120, 130, 140, 150, 160, 170, 180, 190, and 200 kDa each with a Polydispersity Index of between 2 and 3. Each Mw sample was tested at a concentration of 10, 50, 100, 300, and 500 ppm. The Mw of the chitosan sample showing the optimal inhibition of microbial growth (by providing the largest growth inhibition zone (IZ) at 500 ppm) was observed and the results are summarized in Table 1.

TABLE 1

| Microorganism | | Optimal Mw (kDa) | IZ at 500 ppm (mm) |
|---|---|---|---|
| Type | Species | | |
| Bacteria | G− Escherichia coli | 30 | 12 |
| | G− Acetobacter aceti | 40 | 11.7 |
| | G+ Lactobacillus casei | 150 | 10.2 |
| | G+ Listeria innocua | 170 | 12.7 |
| Yeast | Pichia anomala | 20 | 10.5 |
| Yeast | Saccharomyces cerevisiae | 60 | 14.3 |
| Mold | Rhizopus oryzae | 200 | 15 |

Example 5: Antimicrobial Compositions

Based on the above results, the following antimicrobial formulations are prepared:

(a) Broad spectrum anti-microbial chitosan composition

| Mw | % (w/w) |
|---|---|
| 20 | 14.29 |
| 30 | 14.29 |
| 40 | 14.29 |
| 60 | 14.29 |
| 150 | 14.29 |
| 170 | 14.29 |
| 200 | 14.29 |
| | 100.00 |

(b) Broad spectrum anti-microbial chitosan composition with a major focus on Yeast

| Mw | % (w/w) |
|---|---|
| 20 | 30.00 |
| 30 | 8.00 |
| 40 | 8.00 |
| 60 | 30.00 |
| 150 | 8.00 |
| 170 | 8.00 |
| 200 | 8.00 |
| | 100.00 |

(c) Broad spectrum anti-microbial chitosan composition with a minor focus on Yeast

| Mw | % (w/w) |
|---|---|
| 20 | 20.00 |
| 30 | 12.00 |
| 40 | 12.00 |
| 60 | 20.00 |
| 150 | 12.00 |
| 170 | 12.00 |
| 200 | 12.00 |
| | 100.00 |

(d) Broad spectrum anti-microbial chitosan composition with a major focus on Mold

| Mw | % (w/w) |
|---|---|
| 20 | 6.67 |
| 30 | 6.67 |
| 40 | 6.67 |
| 60 | 6.67 |
| 150 | 6.67 |
| 170 | 6.67 |
| 200 | 60.00 |
| | 100.00 |

(e) Broad spectrum anti-microbial chitosan composition with a minor focus on Mold

| Mw | % (w/w) |
|---|---|
| 20 | 11.67 |
| 30 | 11.67 |
| 40 | 11.67 |
| 60 | 11.67 |
| 150 | 11.67 |
| 170 | 11.67 |
| 200 | 30.00 |
| | 100.00 |

(f) Broad spectrum anti-microbial chitosan composition with a major focus on Bacteria

| Mw | % (w/w) |
|---|---|
| 20 | 6.67 |
| 30 | 20.00 |
| 40 | 20.00 |
| 60 | 6.67 |
| 150 | 20.00 |
| 170 | 20.00 |
| 200 | 6.67 |
| | 100.00 |

(g) Broad spectrum anti-microbial chitosan composition with a minor focus on Gram+bacteria

| Mw | % (w/w) |
|---|---|
| 20 | 12.00 |
| 30 | 12.00 |
| 40 | 12.00 |
| 60 | 12.00 |
| 150 | 20.00 |
| 170 | 20.00 |
| 200 | 12.00 |
| | 100.00 |

(h) Broad spectrum anti-microbial chitosan composition with a major focus on Gram−bacteria

| Mw | % (w/w) |
|---|---|
| 20 | 8.00 |
| 30 | 30.00 |
| 40 | 30.00 |
| 60 | 8.00 |

-continued

| Mw | % (w/w) |
|---|---|
| 150 | 8.00 |
| 170 | 8.00 |
| 200 | 8.00 |
| | 100.00 |

(i) Broad spectrum anti-microbial chitosan composition with a minor focus on Gram−bacteria

| Mw | % (w/w) |
|---|---|
| 20 | 12.00 |
| 30 | 20.00 |
| 40 | 20.00 |
| 60 | 12.00 |
| 150 | 12.00 |
| 170 | 12.00 |
| 200 | 12.00 |
| | 100.00 |

(j) Broad spectrum anti-microbial chitosan composition with a major focus on Yeast and Mold

| Mw | % (w/w) |
|---|---|
| 20 | 25.00 |
| 30 | 6.25 |
| 40 | 6.25 |
| 60 | 25.00 |
| 150 | 6.25 |
| 170 | 6.25 |
| 200 | 25.00 |
| | 100.00 |

(k) Broad spectrum anti-microbial chitosan composition with a minor focus on Yeast and Mold

| Mw | % (w/w) |
|---|---|
| 20 | 20.00 |
| 30 | 10.00 |
| 40 | 10.00 |
| 60 | 20.00 |
| 150 | 10.00 |
| 170 | 10.00 |
| 200 | 20.00 |
| | 100.00 |

(l) Broad spectrum anti-microbial chitosan composition with a major focus on Yeast and Mold and Gram+ bacteria

| Mw | % (w/w) |
|---|---|
| 20 | 18.00 |
| 30 | 5.00 |
| 40 | 5.00 |
| 60 | 18.00 |
| 150 | 18.00 |
| 170 | 18.00 |
| 200 | 18.00 |
| | 100.00 |

(m) Broad spectrum anti-microbial chitosan composition with a minor focus on Yeast and Mold and Gram+ bacteria

| Mw | % (w/w) |
|---|---|
| 20 | 15.00 |
| 30 | 12.50 |
| 40 | 12.50 |
| 60 | 15.00 |
| 150 | 15.00 |
| 170 | 15.00 |
| 200 | 15.00 |
| | 100.00 |

(n) Broad spectrum anti-microbial chitosan composition with a major focus on Yeast and Mold and Gram− bacteria

| Mw | % (w/w) |
|---|---|
| 20 | 18.00 |
| 30 | 18.00 |
| 40 | 18.00 |
| 60 | 18.00 |
| 150 | 5.00 |
| 170 | 5.00 |
| 200 | 18.00 |
| | 100.00 |

(o) Broad spectrum anti-microbial chitosan composition with a minor focus on Yeast and Mold and Gram− bacteria

| Mw | % (w/w) |
|---|---|
| 20 | 15.00 |
| 30 | 15.00 |
| 40 | 15.00 |
| 60 | 15.00 |
| 150 | 12.50 |
| 170 | 12.50 |
| 200 | 15.00 |
| | 100.00 |

(p) Anti-microbial chitosan composition with a focus on Yeasts

| Mw | % (w/w) |
|---|---|
| 20 | 50.00 |
| 60 | 50.00 |
| | 100.00 |

(q) Antimicrobial chitosan composition for Yeasts with focus on *Saccharomyces*

| Mw | % (w/w) |
|---|---|
| 20 | 25.00 |
| 60 | 75.00 |
| | 100.00 |

(r) Antimicrobial chitosan composition for Yeasts with focus on *Pichia*

| Mw | % (w/w) |
|---|---|
| 20 | 75.00 |
| 60 | 25.00 |
| | 100.00 |

(s) Antimicrobial chitosan composition for Yeast and Molds

| Mw | % (w/w) |
|---|---|
| 20 | 33.33 |
| 60 | 33.33 |
| 200 | 33.33 |
| | 100.00 |

(t) Antimicrobial chitosan composition for Yeast and Molds with focus on yeasts

| Mw | % (w/w) |
|---|---|
| 20 | 40.00 |
| 60 | 40.00 |
| 200 | 20.00 |
| | 100.00 |

(u) Antimicrobial chitosan composition for Yeast and Molds with focus on molds

| Mw | % (w/w) |
|---|---|
| 20 | 25.00 |
| 60 | 25.00 |
| 200 | 50.00 |
| | 100.00 |

(v) Antimicrobial chitosan composition for Bacteria (Gram+ & −)

| Mw | % (w/w) |
|---|---|
| 30 | 25.00 |
| 40 | 25.00 |
| 150 | 25.00 |
| 170 | 25.00 |
| | 100.00 |

(w) Antimicrobial chitosan composition for Bacteria with a focus on Gram+

| Mw | % (w/w) |
|---|---|
| 30 | 10.00 |
| 40 | 10.00 |
| 150 | 40.00 |
| 170 | 40.00 |
| | 100.00 |

(x) Antimicrobial chitosan composition for Bacteria with focus on Gram−

| Mw | % (w/w) |
|---|---|
| 30 | 40.00 |
| 40 | 40.00 |
| 150 | 10.00 |
| 170 | 10.00 |
| | 100.00 |

(y) Antimicrobial chitosan composition for Yeast and Molds and Gram+bacteria

| Mw | % (w/w) |
|---|---|
| 20 | 20.00 |
| 60 | 20.00 |
| 200 | 20.00 |
| 150 | 20.00 |
| 170 | 20.00 |
| | 100.00 |

(z) Antimicrobial chitosan composition for Yeast and Molds and Gram+bacteria with a focus on Yeasts

| Mw | % (w/w) |
|---|---|
| 20 | 35.00 |
| 60 | 35.00 |
| 200 | 10.00 |
| 150 | 10.00 |
| 170 | 10.00 |
| | 100.00 |

(aa) Antimicrobial chitosan composition for Yeast and Molds and Gram+bacteria with a focus on Yeasts and Molds

| Mw | % (w/w) |
|---|---|
| 20 | 25.00 |
| 60 | 25.00 |
| 200 | 25.00 |
| 150 | 12.50 |
| 170 | 12.50 |
| | 100.00 |

(bb) Antimicrobial chitosan composition for Yeast and Molds and Gram+bacteria with a focus on Molds

| Mw | % (w/w) |
|---|---|
| 20 | 10.00 |
| 60 | 10.00 |
| 200 | 60.00 |
| 150 | 10.00 |
| 170 | 10.00 |
| | 100.00 |

(cc) Antimicrobial chitosan composition for Yeast and Molds and Gram+bacteria with a focus on Gram+

| Mw | % (w/w) |
|---|---|
| 20 | 13.33 |
| 60 | 13.33 |
| 200 | 13.33 |
| 150 | 30.00 |
| 170 | 30.00 |
| | 100.00 |

(dd) Antimicrobial chitosan composition for Yeast and Molds and Gram+bacteria with a focus on *Saccharomyces*

| Mw | % (w/w) |
|---|---|
| 20 | 12.50 |
| 60 | 50.00 |
| 200 | 12.50 |
| 150 | 12.50 |
| 170 | 12.50 |
| | 100.00 |

(ee) Antimicrobial chitosan composition for Yeast and Bacteria

| Mw | % (w/w) |
|---|---|
| 20 | 25.00 |
| 60 | 25.00 |
| 30 | 12.50 |
| 40 | 12.50 |
| 150 | 12.50 |
| 170 | 12.50 |
| | 100.00 |

(ff) Antimicrobial chitosan composition for Yeast and Bacteria with a focus on Yeast

| Mw | % (w/w) |
|---|---|
| 20 | 25.00 |
| 60 | 25.00 |
| 30 | 12.50 |
| 40 | 12.50 |
| 150 | 12.50 |
| 170 | 12.50 |
| | 100.00 |

(gg) Antimicrobial chitosan composition for Yeast and Bacteria with a focus on Bacteria

| Mw | % (w/w) |
|---|---|
| 20 | 10.00 |
| 60 | 10.00 |
| 30 | 20.00 |
| 40 | 20.00 |
| 150 | 20.00 |
| 170 | 20.00 |
| | 100.00 |

(hh) Antimicrobial chitosan composition for Yeast and Bacteria with a focus on Gram+bacteria

| Mw | % (w/w) |
|---|---|
| 20 | 7.50 |
| 60 | 7.50 |
| 30 | 7.50 |
| 40 | 7.50 |
| 150 | 35.00 |
| 170 | 35.00 |
| | 100.00 |

(ii) Antimicrobial chitosan composition for Yeast and Bacteria with a focus on Gram−bacteria

| Mw | % (w/w) |
|---|---|
| 20 | 7.50 |
| 60 | 7.50 |
| 30 | 35.00 |
| 40 | 35.00 |
| 150 | 7.50 |
| 170 | 7.50 |
| | 100.00 |

(jj) Antimicrobial chitosan composition for Yeast and Bacteria with a focus on Gram−bacteria and yeast

| Mw | % (w/w) |
|---|---|
| 20 | 20.00 |
| 60 | 20.00 |
| 30 | 20.00 |
| 40 | 20.00 |
| 150 | 10.00 |
| 170 | 10.00 |
| | 100.00 |

(kk) Antimicrobial chitosan composition for Yeast and Bacteria with a focus on Gram+bacteria and yeast

| Mw | % (w/w) |
|---|---|
| 20 | 20.00 |
| 60 | 20.00 |
| 30 | 10.00 |
| 40 | 10.00 |
| 150 | 20.00 |
| 170 | 20.00 |
| | 100.00 |

(ll) Antimicrobial chitosan composition for Yeast and Bacteria with a focus on Gram−bacteria and yeast

| Mw | % (w/w) |
|---|---|
| 20 | 20.00 |
| 60 | 20.00 |
| 30 | 20.00 |
| 40 | 20.00 |
| 150 | 10.00 |
| 170 | 10.00 |
| | 100.00 |

(mm) Antimicrobial chitosan composition for Yeast and Molds and Gram−bacteria

| Mw | % (w/w) |
|---|---|
| 30 | 20.00 |
| 40 | 20.00 |
| 20 | 20.00 |
| 60 | 20.00 |
| 200 | 20.00 |
| | 100.00 |

(nn) Antimicrobial chitosan composition for Yeast and Molds and Gram−bacteria with a focus on Yeasts

| Mw | % (w/w) |
|---|---|
| 30 | 35.00 |
| 40 | 35.00 |
| 20 | 10.00 |
| 60 | 10.00 |
| 200 | 10.00 |
| | 100.00 |

(oo) Antimicrobial chitosan composition for Yeast and Molds and Gram−bacteria with a focus on Yeasts and Molds

| Mw | % (w/w) |
|---|---|
| 30 | 12.50 |
| 40 | 12.50 |
| 20 | 25.00 |
| 60 | 25.00 |
| 200 | 25.00 |
| | 100.00 |

(pp) Antimicrobial chitosan composition for Yeast and Molds and Gram−bacteria with a focus on Molds

| Mw | % (w/w) |
|---|---|
| 30 | 10.00 |
| 40 | 10.00 |
| 20 | 10.00 |
| 60 | 10.00 |
| 200 | 60.00 |
| | 100.00 |

(qq) Antimicrobial chitosan composition for Yeast and Molds and Gram−bacteria with a focus on Gram−

| Mw | % (w/w) |
|---|---|
| 30 | 30.00 |
| 40 | 30.00 |
| 20 | 13.33 |
| 60 | 13.33 |
| 200 | 13.33 |
| | 100.00 |

(rr) Antimicrobial chitosan composition for Yeast and Molds and Gram−bacteria with a focus on *Saccharomyces*

| Mw | % (w/w) |
|---|---|
| 30 | 12.50 |
| 40 | 12.50 |
| 20 | 12.50 |
| 60 | 50.00 |
| 200 | 12.50 |
| | 100.00 |

(ss) Antimicrobial chitosan composition for Gram+bacteria

| Mw | % (w/w) |
|---|---|
| 150 | 50.00 |
| 170 | 50.00 |
| | 100.00 |

(tt) Antimicrobial chitosan composition for Gram−bacteria

| Mw | % (w/w) |
|---|---|
| 30 | 50.00 |
| 40 | 50.00 |
| | 100.00 |

The invention claimed is:

1. An antimicrobial composition consisting essentially of chitosan polymers having an average Mw of about 30 kDa, about 40 kDa, about 150 kDa and about 170 kDa, and wherein the composition targets bacteria.

2. The antimicrobial composition of claim 1, wherein chitosan polymers having an average Mw of about 150 kDa and/or about 170 kDa are present in substantially greater amounts in percent by weight, wherein substantially greater amounts in percent by weight means that the chitosan polymer is present in the composition in amounts that are about 10 percentage points (w/w) to about 30 percentage points (w/w) greater than other chitosan polymers in the composition.

3. The antimicrobial composition of claim 1 wherein chitosan polymers having an average Mw of about 30 kDa and/or about 40 kDa are present in substantially greater amounts, wherein substantially greater amounts in percent by weight means that the chitosan polymer is present in the composition in amounts that are about 10 percentage points (w/w) to about 30 percentage points (w/w) greater than other chitosan polymers in the composition.

4. An antimicrobial composition consisting essentially of chitosan polymers having an average Mw of about 30 kDa, about 40 kDa, about 150 kDa, about 170 kDa and about 200 kDa.

5. The antimicrobial composition of claim 1, wherein the chitosan polymer is from a fungus, crustacean or an insect.

6. The antimicrobial composition of claim 5, wherein the chitosan polymer is from a fungus.

7. The antimicrobial composition of claim 6, wherein the chitosan polymer is from a mushroom.

8. The antimicrobial composition of claim 1, wherein composition is in the form of a powder, liquid solution or suspension.

9. The antimicrobial composition of claim 8, wherein composition is in the form of a powder.

10. A product comprising the compositions of claim 1, wherein the product is a food, beverage, cosmetic, personal care item, medical device or pharmaceutical.

11. A method of inhibiting bacterial growth in a product comprising incorporating an effective amount of the compositions of claim 1 into the product.

12. The antimicrobial composition of claim 1, wherein the chitosan polymers having a Mw selected from about 30 kDa and about 170 kDa are present in substantially greater amounts in percent by weight of, wherein substantially greater amounts in percent by weight means that the chitosan polymer is present in the composition in amounts that are about 10 percentage points (w/w) to about 30 percentage points (w/w) greater than other chitosan polymers in the composition.

\* \* \* \* \*

UNITED STATES PATENT AND TRADEMARK OFFICE
CERTIFICATE OF CORRECTION

PATENT NO. : 11,882,832 B2
APPLICATION NO. : 17/940420
DATED : January 30, 2024
INVENTOR(S) : David Brown et al.

Page 1 of 1

It is certified that error appears in the above-identified patent and that said Letters Patent is hereby corrected as shown below:

In the Claims

At Claim 11, Column 21, Lines 10-11 "compositions" should read -- composition --.

Signed and Sealed this
Thirty-first Day of December, 2024

Derrick Brent
*Acting Director of the United States Patent and Trademark Office*